(12) United States Patent
Nicolas et al.

(10) Patent No.: US 6,827,489 B2
(45) Date of Patent: Dec. 7, 2004

(54) LOW-DOSE EXPOSURE AIDED POSITIONING (LEAP) FOR DIGITAL RADIOGRAPHY

(75) Inventors: Francois Serge Nicolas, Wauwatosa, WI (US); Vincent S. Polkus, Delafield, WI (US); Kenneth Scott Kump, Waukesha, WI (US); Remy Andre Klausz, Neuilly-sur-Seine (FR)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 3 days.

(21) Appl. No.: 10/003,490

(22) Filed: Nov. 1, 2001

(65) Prior Publication Data

US 2003/0081734 A1 May 1, 2003

(51) Int. Cl.[7] .................................................. A61B 6/08
(52) U.S. Cl. ....................... 378/205; 378/20; 378/62; 378/68; 378/69
(58) Field of Search ............................. 378/20, 62, 65, 378/68, 69, 205

(56) References Cited

U.S. PATENT DOCUMENTS

| | | | | |
|---|---|---|---|---|
| 4,633,494 A | * | 12/1986 | Klausz | 378/205 |
| 5,218,625 A | | 6/1993 | Heidsieck | 378/97 |
| 5,295,200 A | * | 3/1994 | Boyer | 382/280 |
| 6,282,264 B1 | * | 8/2001 | Smith et al. | 378/189 |
| 6,366,638 B1 | | 4/2002 | Hsieh et al. | |

FOREIGN PATENT DOCUMENTS

| | | |
|---|---|---|
| DE | 196 28 675 | 1/1998 |
| EP | 0 761 166 | 3/1977 |
| WO | WO 01/26132 | 4/2001 |
| WO | WO 01/40754 | 6/2001 |

* cited by examiner

Primary Examiner—Edward J. Glick
Assistant Examiner—Courtney Thomas
(74) Attorney, Agent, or Firm—McAndrews, Held & Malloy, Ltd.; Peter J. Vogel; Michael A. Dellapenna

(57) ABSTRACT

A system and method for improved imaging of a patient through the use of low-dose exposure aided positioning is provided. The patient is positioned in the X-ray system and them imaged with a low-dose pre-shot to verify the positioning of the patient. If the patient's positioning is acceptable, the patient is then imaged with a full-dose X-ray exposure. If the patient's positioning is not acceptable, the patient is repositioned and re-imaged with a low-dose pre-shot until the patient's positioning is acceptable. The low-dose pre-shot may take the form of a low-dose X-ray imaging sequence. The present invention thus provides for rapid verification of the proper positioning of the patient in the X-ray system in order to provide for optimal X-ray image quality. Additionally, the X-ray imaging system thus minimizes the additional exposure to X-ray radiation on the part of the patient.

29 Claims, 2 Drawing Sheets

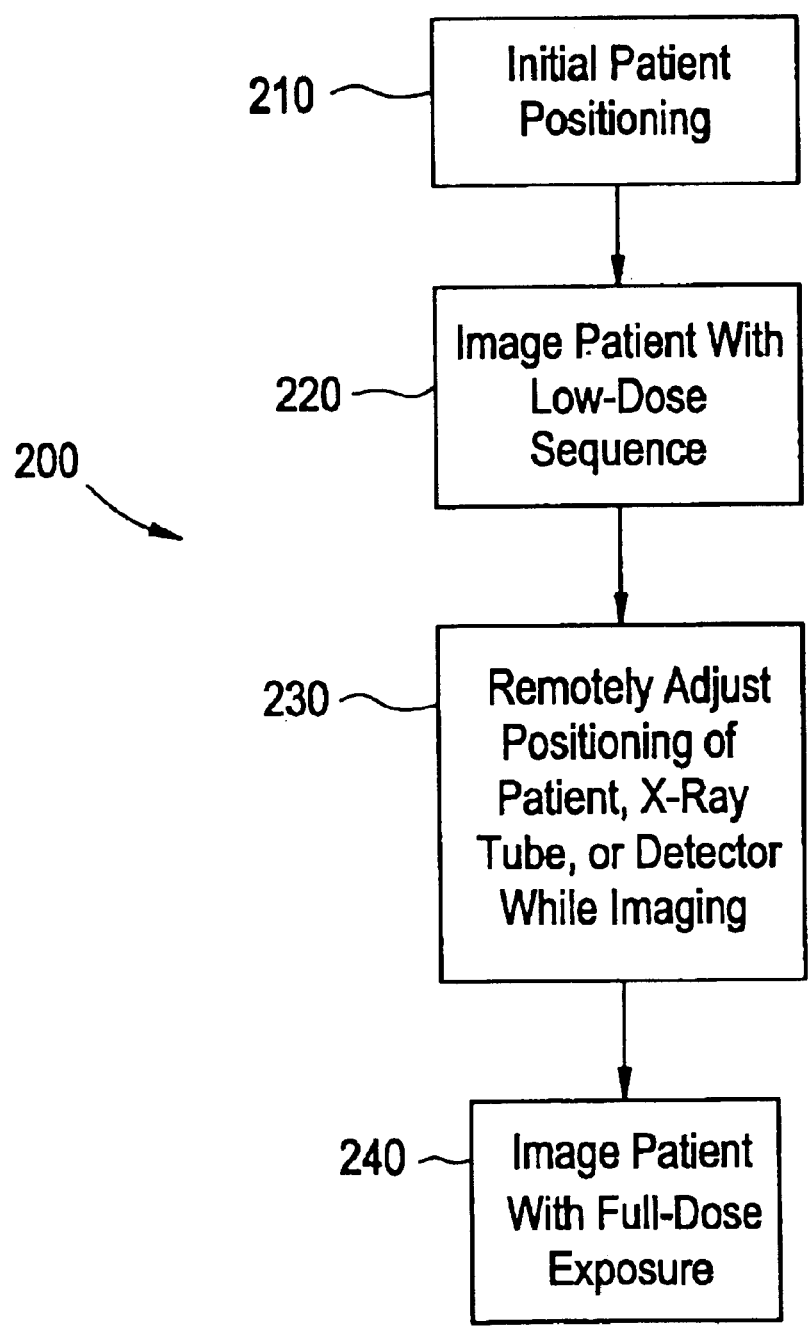

LOW-DOSE EXPOSURE AIDED POSITIONING (LEAP) FOR DIGITAL RADIOGRAPHY

BACKGROUND OF THE INVENTION

The preferred embodiments of the present invention generally relate to improvements in a medical X-ray imaging system. More particularly, the present invention relates to a system and method for improved imaging of a patient through the use of low-dose exposure aided positioning.

Presently, to perform X-ray imaging, a patient is first positioned and then the X-ray image is acquired. During clinical use, however, it is often the case that later review of the X-ray images reveals an error in the X-ray image, for example, the patient may be improperly positioned. Once the error in the X-ray image has been discovered, the patient must then be re-positioned and another X-ray image acquired.

Unfortunately, many X-ray imaging systems rely on analog film. The quality of the X-ray image on the analog film may only be observed after the analog film has been developed and processed. Typically, developing the analog film requires several minutes at least, during which time, the patient may have left the examination room, for example, or may otherwise be unavailable. If the X-ray image is found to be less then optimal, the patient may need to be recalled and re-positioned. Recalling and re-positioning the patient may be a time consuming process which may in turn affect the throughput of the X-ray system and consequently the overall profitability of the X-ray system.

Other systems besides analog film systems also suffer from this drawback. Computed Radiography (CR) requires reading the cassette before the positioning accuracy and image quality of the X-ray image may be ascertained.

Additionally, re-acquiring the X-ray image exposes the patient to additional X-rays. Although the exposure of the patient to additional X-rays is necessary to acquire the new X-ray image, medical guidelines and concerns for patient safety require the operator to maintain the number of exposures to X-ray radiation that a patient may undergo during any set time to be as low as reasonably achievable (ALARA). Thus, the exposure of the patient to additional X-ray radiation is undesirable from a patient safety perspective.

Thus, a need has long existed for an improved X-ray imaging system that provides for rapid verification of the proper positioning of a patient in an X-ray image. A need has also existed for such an X-ray imaging system that minimizes the additional exposure of X-rays to the patient.

BRIEF SUMMARY OF THE INVENTION

The preferred embodiments of the present invention include a system and method for improved imaging of a patient through the use of low-dose exposure aided positioning. First, the patient is positioned in the X-ray system and imaged with a low-dose pre-shot. Then, the low-dose pre-shot is analyzed to verify or correct the positioning of the patient in the X-ray system. Once the patient is properly positioned, the patient is imaged with a full-dose X-ray exposure. Instead of a single low-dose pre-shot, the patient may be imaged with a low-dose X-ray imaging sequence and the positioning of the patient may be adjusted during the sequence.

BRIEF DESCRIPTION OF THE DRAWINGS

FIG. 2 illustrates a flowchart of an alternative embodiment of the present invention called RAD scout view.

DETAILED DESCRIPTION OF THE INVENTION

Figure 1:
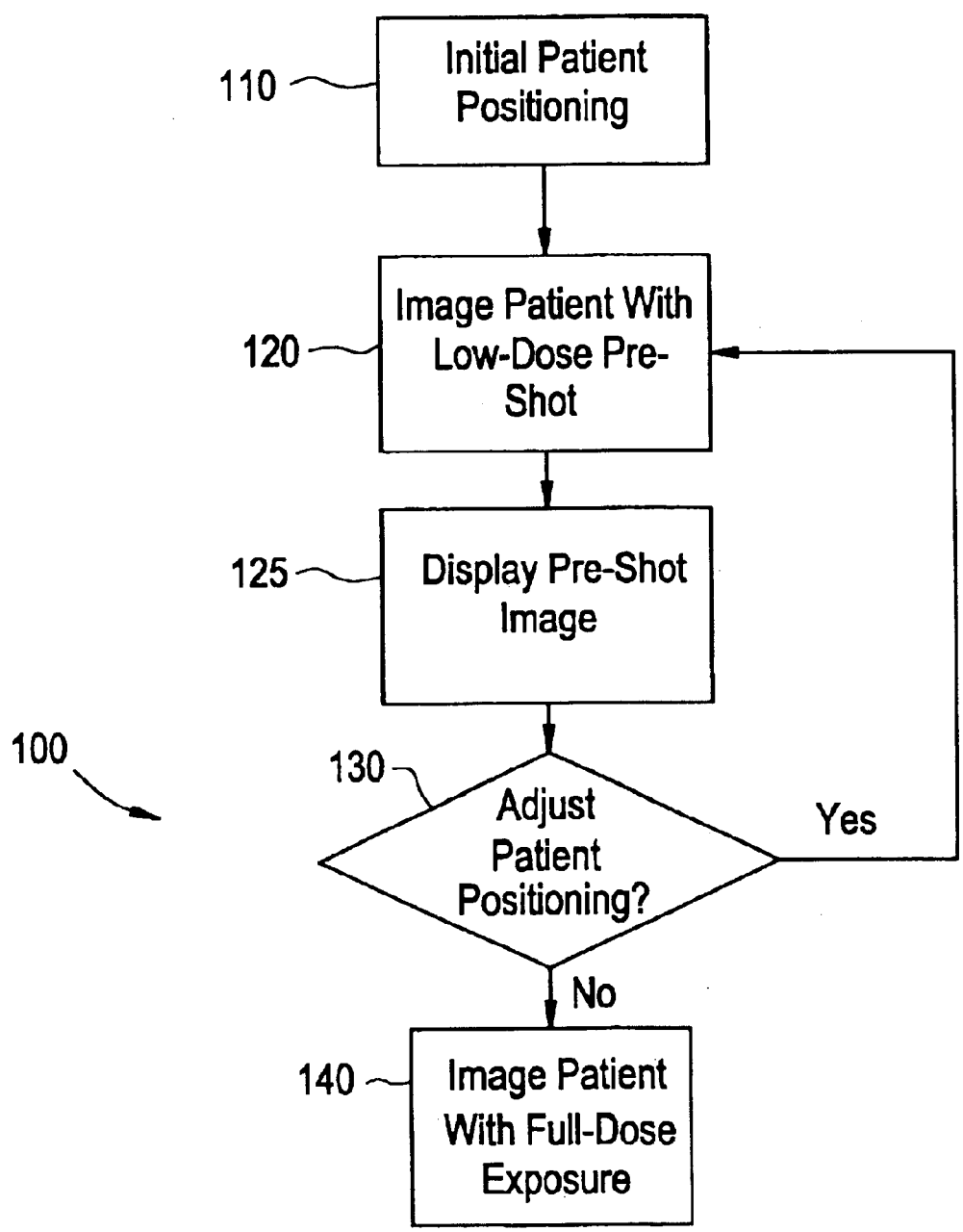
FIG. 1 illustrates a flow chart of Low dose Exposure Aided Positioning (LEAP) according to a preferred embodiment of the present invention.

FIG. 1 illustrates a flow chart 100 of Low dose Exposure Aided Positioning (LEAP) according to a preferred embodiment of the present invention. The LEAP of the present invention is preferably implemented on a digital X-ray imaging system such as the Revolution™ XQ/i digital product from General Electric (GE). Using the Revolution™, the time between acquisition of the X-ray image and verification of the quality of the X-ray image is reduced.

That is, the Revolution™ displays a preview image in approximately 6 seconds or less (most preferably in less than one second), while a processed image may be displayed in approximately 20 seconds or less. As further described below, a preview image is a preliminary image that may provide an initial image of the patient. For example, the preliminary image may be determined by only processing a reduced resolution image, for example, a 2×2 or 4×4 binned pixel image. The processed image is an X-ray image in which every X-ray pixel has been processed and displayed.

The preview image may thus be employed to verify and correct patient positioning. The patient may then be rapidly re-positioned and re-imaged, if desired, to correct poor patient positioning in the original image. Consequently, an image with unacceptable quality will not be printed (or sent to a Picture Archiving and Communication System (PACS)), and a new acquisition may be performed while the patient is still in the X-ray system, and most likely still approximately positioned.

Referring to the flowchart 100, first, at step 110 the patient and/or X-ray tube and/or detector is positioned in the X-ray system.

Next, at step 120, the patient is imaged with a low-dose pre-shot. That is, a X-ray image of the patient is acquired using a lower X-ray dose that is typically used for imaging. The low dose is preferably around 1–4% of the typical X-ray imaging dose. The X-ray technique parameters may be the same or different then the full dose image. These technique parameters are preferably pre-set and placed into a table which may be indexed by factors such as anatomical view and patient age.

At step 125, the pre-shot image is displayed or the accuracy of the patient positioning is calculated as further described below.

Next, at step 130, the decision whether or not to adjust the patient positioning is made. In the preferred embodiment, this decision is made visually by the operator and signified with a button press on the input device. That is, the operator observes the pre-shot image and makes a decision whether or not to reposition the patient.

Alternatively, a computer algorithm may be used to make the decision whether or not to reposition the patient. For example, the computer algorithm may use image segmentation to detect whether a selected anatomy is in the field of view of the X-ray detector. That is, when the patient is first positioned, the operator selects the type of X-ray image to be taken from among a menu of available image types. For example, the operator may select "hand" from the menu when the operator desires to image a patient's hand. The patient is then imaged with the low-dose pre-shot. The resultant low-dose image is then processed via a computer algorithm, such as segmentation for example, to determine the positioning of the patient within the image. That is, the computer algorithm analyzes the low-dose image and recognizes the positioning of the patient, for instance, by identifying the relative locations of landmarks within the image. If the computer algorithm determines that the positioning of the patient is acceptable, the final, high-dose image is taken. If the computer algorithm does not determine that the positioning of the patient is acceptable, the computer algorithm prompts the operator for a decision as to whether or not to perform the high-dose imaging. Further disclosure with regard to image segmentation and auto recognition computer algorithms may be found in the following patent applications: "Method and Apparatus For Determining a Dynamic Range of a Digital Medical Image" listing Kenneth Kump as inventor and having application Ser. No. 09/344, 190; "Medical Diagnostic Method and Apparatus To Control Dual Energy Exposure Techniques Based On Image Information" listing Chris Unger and Ken Kump as inventors and having application Ser. No. 09/739,127; and "Pre Exposure Image Used For Saturation Management" listing Claire Chichereau and Francois Nicholas as inventors and having application Ser. No. 09/619,249.

Returning to step 130, at step 130 the position of the patient is adjusted if necessary. That is, once the low dose preview image has been acquired, the positioning of the patient may be verified by the X-ray technician and the technician may direct the patient to be re-positioned if necessary. Alternatively, the X-ray tube and/or the X-ray detector may be repositioned. Once the patient has been re-positioned, the patient may be imaged again with the low-dose pre-shot to verify the patient's position. The patient may be repeatedly re-positioned until the technician is satisfied with the patient's position. The total dose of X-ray radiation that the patient may be exposed to during repeated positioning and X-ray image verification steps is considerably lower than a full imaging dose.

Finally, at step 140, the patient is imaged with a full-dose exposure. That is, once the position of the patient has been verified, the full-dose X-ray exposure is acquired.

Preferably, the technician controls the X-ray system and selects the X-ray imaging protocol from a remote acquisition console. The acquisition technique for the low dose pre-shot is preferably automatically selected by the X-ray system. The LEAP image is preferably displayed in less than one second to allow the technician to verify patient positioning. The low-dose pre-shot is well-suited to X-ray systems without remote control of the X-ray tube, X-ray detector, or X-ray table.

The LEAP of the present invention may be employed to greatly minimize the additional radiation dose received by the patient through repeated imaging due to improper patient positioning.

FIG. 2 illustrates a flowchart 200 of an alternative embodiment of the present invention called RAD scout view. The RAD scout view of the present invention may be implemented in an X-ray system that allows the acquisition of a sequence of images at a low frame rate and also allows the technician to re-position in the X-ray imaging system (the tube, table and/or detector) during the acquisition of the imaging sequence.

Referring to the flowchart 200, first, at step 210, the patient is positioned on the X-ray table of the X-ray imaging system.

Next, at step 220, the patient is imaged with a low dose sequence at a low frame rate of preferably five frames/second. Alternatively, the patient may be imaged at a much slower rate of approximately one frame every five seconds to allow the patient to be repositioned between frames.

At step 230, while the patient is being imaged at a low frame rate, the technician controls the position of the X-ray tube, table, and/or detector, to adjust the positioning of the patient. That is, a sequence of images of the patient is acquired and displayed in real time while the technologist adjusts the system geometry.

Finally, at step 240, once the technician has positioned the patient into the desired orientation, the technician stops the low dose sequence and images the patient with a full-dose exposure. RAD scout view thus provides for optimizing the positioning of the patient in a dynamic way.

In order to allow the X-ray system to produce X-ray images at a rate of 5 images/second, the image data flow of the X-ray system may be altered to provide for increased transfer speed and reduced processing time.

For example, the X-ray image data may be sub-sampled, preferably by pixel binning, often simply referred to as binning. Binning the X-ray imaging data involves reducing the overall image data by representing a number of pixels in the original image with a single pixel for processing. For example, first the X-ray signal passing through the patient is received by the X-ray detector. The surface of the X-ray detector is subdivided into a large number of pixels, each pixel may record a value for the X-ray signal level it receives independent of the other pixels. The value for the X-ray signal level received by a group of pixels (preferably four, nine, or sixteen pixels) may be averaged to form a single value and then further processed. Thus, the total number of X-ray signal level values that must be processed to provide and X-ray image may be reduced by a factor of four, nine, or sixteen, depending on implementation. By reducing the total data needing to be processed before an X-ray image is displayed, binning minimizes the processing time necessary to process the X-ray image. The binning preferably occurs in the X-ray detector itself, or may alternatively occur once the X-ray signal levels are read from the detector.

Alternatively, the X-ray image data may be sub-sampled by sparsing. Sparsing involves simply choosing the X-ray signal level of one pixel out of the group of preferably four, nine, or sixteen pixels and then attributing the value of the one pixel to the spatial area of the group.

The preferred embodiments of the present invention thus provide several advantages. For example, the positioning of that patient in the X-ray system may be rapidly verified. Also, because the low-dose pre-shot is employed to verify the patient's positioning and then a single high-dose exposure is triggered, the exposure of the patient to the additional high-dose X-ray exposures due to re-imaging improperly positioned patients is eliminated. Additionally, the general quality of patient positioning may be improved because the retake procedure is much simpler and because the dose due to re-imaging is not doubled. Thus, a technician may be more likely to improve the positioning if the low-dose image shows it is of medium quality while the technician may have accepted the medium-quality image (rather than re-exposing for a high-quality image) with the previous systems because of the additional radiation exposure to the patient.

Additionally, the low-dose exposures of the low-dose pre-shot or low-dose sequence of the present invention may be employed to optimize imaging parameters for the high-dose exposure. For example, the low-dose exposure may be used to provide zero point parameters, saturation management parameters, field of view optimization parameters, or spatial physical filter parameters.

With regard to zero point parameters, zero point parameters are parameters that are automatically determined by the imaging equipment itself in response to the low-dose exposure. For example, zero point parameters may include X-ray tube current, exposure time for X-ray, X-ray tube voltage, focal spot, or other X-ray parameters. Additionally, automatically processing the low-dose image may be used to determine the thickness of the patient as well as the patient's composition. Once the thickness and composition are known, the X-ray image acquisition parameters of the high-dose exposure may be optimized to provide the best view. For example, once the thickness of the patient is known, the dynamic range of the X-ray system may be altered to provide the greatest detail of the region of interest.

With regard to saturation management parameters, when imaging thin tissues such as a hand, for example, the X-ray detector may saturate with a normal dose. To prevent saturation, the low-dose image may be analyzed and then pasted back with the full-dose image thus virtually extending the saturation range of the detector.

With regard to field of view optimization parameters, the technician may select the region of interest from the low-dose image. Then, the X-ray system may be positioned to automatically move to the center of the region of interest as well an minimize the region of interest before acquiring the full-dose shot. Centering and minimizing the field of view of the X-ray image to the region of interest may reduce the dose to the patient.

With regard to spatial physical filter parameters, the low dose image may be processed to determine the thickness of the patient over the image. The average thickness data may then be supplied to the collimator, which may then filter the field of view spatially. That is, the collimator may be activated to deliver a lower dose to thinner regions and a higher dose to thicker regions. Matching dose to region thickness may yield a better image quality as well as a lower overall dose to the patient. For example, the image quality may be improved because adjustment to different anatomical structures may improve the Signal-To-Noise Ratio (SNR) of the X-ray image.

While the invention has been described with reference to a preferred embodiment, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. A method for improving the quality of X-ray images generated by an X-ray imaging system, said X-ray system including an X-ray emitter and an X-ray detector, said method including the steps of:
   positioning the patient between said X-ray emitter and said X-ray detector;
   imaging the patient with a low-dose pre-shot to determine a low-dose image,
   wherein the radiation dose level of said low-dose pre-shot is less than the radiation dose level of a full-dose exposure,
   wherein said imaging includes imaging the patient with a low-dose X-ray imaging sequence;
   analyzing the low dose image to determine the positioning of the patient relative to said X-ray emitter and said X-ray detector;
   adjusting the positioning of the patient relative to at least one of said X-ray emitter and said X-ray detector; and
   imaging the patient with a full-dose exposure.

2. The method of claim 1 wherein said adjusting step includes adjusting the positioning of the patient and then re-imaging said patient with a second low-dose pre-shot prior to imaging the patient with a full-dose exposure.

3. The method of claim 1 wherein said low-dose pre-shot has a dose of less than 10 percent of said full-dose exposure.

4. The method of claim 1 wherein said low-dose pre-shot has a dose of less than 4 percent of said full-dose exposure.

5. The method of claim 1 wherein said X-ray system includes X-ray imaging parameters and said X-ray imaging parameters vary between said low-dose pre-shot and said full-dose exposure.

6. The method of claim 1 wherein said X-ray imaging parameters are varied according to one of patient size and anatomical view.

7. The method of claim 1 wherein the X-ray system is controlled by a technician from a remote acquisition console.

8. The method of claim 1 wherein the X-ray system is controlled automatically.

9. The method of claim 1 wherein said low-dose pre-shot generates an image within 5 seconds.

10. The method of claim 1 wherein said low dose pre-shot generates an image within one second.

11. The method of claim 1 wherein said low-dose imaging sequence occurs at a frame rate of approximately 5 frames per second.

12. The method of claim 1 wherein said low-dose imaging sequence occurs at a frame rate of approximately 1 frame every 5 seconds.

13. The method of claim 1 wherein the X-ray images in the X-ray imaging sequence are sub-sampled prior to processing.

14. The method of claim 13 wherein the X-ray images of the X-ray imaging sequence are sub-sampled using binning.

15. The method of claim 13 wherein the X-ray images of the X-ray imaging sequence are sub-sampled using sparsing.

16. The method of claim 1 wherein said analyzing step further includes automatically analyzing said low-dose image using a computer algorithm,
   wherein said computer algorithm employs image segmentation to determine the positioning of the patient.

17. A method for verifying the positioning of a patient in an X-ray imaging system before imaging the patient with a full-dose X-ray exposure including the steps of:
   positioning the patient in the X-ray system;
   imaging the patient with a low-dose pre-shot, wherein the radiation dose level of said low-dose pre-shot is less than the radiation dose level of a full-dose exposure,
   wherein said imaging includes imaging the patient with a low-dose X-ray imaging sequence; and
   verifying the positioning of the patient in the X-ray system via the low-dose pre-shot image before imaging the patient with a full-dose X-ray exposure.

18. The method of claim 17 wherein said verifying step includes adjusting the positioning of the patient and then re-imaging said patient with a second low-dose pre-shot prior to imaging the patient with a full-dose exposure.

19. The method of claim 17 wherein said low dose pre-shot uses a dose of 1 to 4 percent of the dose of the full-dose exposure.

20. The method of claim 17 wherein the X-ray system is controlled by a technician from a remote acquisition console.

21. The method of claim 17 wherein said low-dose pre-shot generates an image within 5 seconds.

22. The method of claim 17 wherein said low dose pre-shot generates an image within one second.

23. The method of claim 17 wherein said low-dose imaging sequence occurs at a frame rate of approximately 5 frames per second.

24. The method of claim 17 wherein said low-dose imaging sequence occurs at a frame rate of approximately 1 frame every 5 seconds.

25. The method of claim 17 wherein the X-ray images in the X-ray imaging sequence are sub-sampled prior to processing.

26. The method of claim 25 wherein the X-ray images of the X-ray imaging sequence are sub-sampled by binning.

27. The method of claim 25 wherein the X-ray images of the X-ray imaging sequence are sub-sampled by sparsing.

28. The method of claim 17 wherein said verifying step includes automatically verifying said low-dose image using a computer algorithm, wherein said computer algorithm employs image segmentation to determine the positioning of the patient.

29. A method for improving the quality of X-ray images generated by an X-ray imaging system, said method including the steps of:

positioning a patient in the X-ray system;

imaging the patient with a low-dose pre-shot, wherein the radiation dose level of said low-dose pre-shot is less than the radiation dose level of a full-dose exposure; and processing the low-dose pre-shot image to provide imaging parameters to be employed during a subsequent X-ray exposure, wherein said imaging parameters include at least one of zero point parameters, saturation management parameters, field of view optimization parameters and spatial physical filter parameters.

* * * * *